(12) United States Patent
Knudsen et al.

(10) Patent No.: US 8,853,157 B2
(45) Date of Patent: Oct. 7, 2014

(54) METHODS OF TREATING STEROID-INDUCED OBESITY USING GLP-1 AGONISTS

(71) Applicant: Novo Nordisk A/S, Bagsvaerd (DK)

(72) Inventors: Sanne Moeller Knudsen, Vaerloese (DK); Karin Rimvall, Hoersholm (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

(21) Appl. No.: 13/776,839

(22) Filed: Feb. 26, 2013

(65) Prior Publication Data

US 2013/0165370 A1    Jun. 27, 2013

Related U.S. Application Data

(63) Continuation of application No. 11/629,238, filed as application No. PCT/EP2005/052475 on May 31, 2005, now Pat. No. 8,410,047.

(60) Provisional application No. 60/628,418, filed on Nov. 16, 2004.

(30) Foreign Application Priority Data

Jun. 11, 2004  (DK) ................................ 2004 00911

(51) Int. Cl.
*A61P 3/06*   (2006.01)
*A61K 38/26*  (2006.01)
*A61K 31/56*  (2006.01)
*A61K 38/00*  (2006.01)
*A61K 31/26*  (2006.01)

(52) U.S. Cl.
CPC ................. *A61K 38/00* (2013.01); *A61K 31/56* (2013.01); *A61K 31/26* (2013.01); *A61K 38/26* (2013.01)
USPC ............................................ 514/7.2; 514/4.8

(58) Field of Classification Search
None
See application file for complete search history.

(56) References Cited

U.S. PATENT DOCUMENTS

| | | | |
|---|---|---|---|
| 6,004,297 A | 12/1999 | Steenfeldt-Jensen et al. | |
| 6,191,102 B1 | 2/2001 | DiMarchi et al. | |
| 6,268,343 B1 | 7/2001 | Knudsen et al. | |
| 6,458,924 B2 | 10/2002 | Knudsen et al. | |
| 6,844,321 B2 | 1/2005 | Arentsen | |
| 6,939,853 B2 | 9/2005 | Knudsen et al. | |
| 7,235,627 B2 | 6/2007 | Knudsen et al. | |
| 8,097,698 B2 | 1/2012 | Knudsen et al. | |
| 2002/0187926 A1* | 12/2002 | Knudsen et al. | 514/2 |
| 2003/0199672 A1 | 10/2003 | Knudsen et al. | |
| 2004/0002442 A1 | 1/2004 | Pan et al. | |
| 2004/0106547 A1 | 6/2004 | Larsen et al. | |

FOREIGN PATENT DOCUMENTS

| | | |
|---|---|---|
| EP | 338806 | 10/1989 |
| EP | 897728 | 2/1999 |
| WO | 9808871 A1 | 3/1998 |
| WO | 98/19698 | 5/1998 |
| WO | 98/20895 | 5/1998 |
| WO | 01/57084 A1 | 8/2001 |
| WO | 0172361 | 10/2001 |
| WO | 03/002136 | 1/2003 |
| WO | 03/057235 | 7/2003 |
| WO | 03/058203 | 7/2003 |
| WO | 03/059378 A2 | 7/2003 |
| WO | 03/103572 | 12/2003 |
| WO | 2004/002556 A1 | 1/2004 |
| WO | 2004/050115 A2 | 6/2004 |

OTHER PUBLICATIONS

Achiron et al., Eur. Neuropsychopharmacology, 9: 111-113, 1999.*
Fransson et al., Diabetes and Metabolic syndrome 6: 1-13, 2014.*
Diabetes Care, Consensus Development Conference on Antipsychotic Drugs and Obesity and Diabetes, 2004, vol. 27, No. 2, pp. 596-601.
Baptista, "Body Weight Gain Induced by Antipsychotic Drugs: Mechanisms and Management", Acta Psychiatr. Scand., 1999, vol. 100, pp. 3-16.
Bjenning et al., "NN2211, A Protracted GLP-1 Derivative", Diabetes Research and Clinical Practice, 2000, vol. 50, No. 1, p. S386.
Case et al., "The Potential Role of Appetite in Predicting Weight Changes During Treatment With Olanzapine", BMC Psychiatry, 2010, vol. 10, No. 72, pp. 1-9.
Coccurello et al., "Chronic Administration of Olanzapine Affects Behavioral Satiety Sequence and Feeding Behavior in Female Mice", Eat Weight Disorder, 2008, vol. 13, No. 3, pp. e55-60.
Delgado-Aros et al., "Effect of GLP-1 on Gastric Volume, Emptying, Maximum Volume Ingested, and Postprandial Symptoms in Humans", Amierican Journal of Physiology—Gastrointestinal and Liver, 2002, vol. 282, pp. G424-G431.
Edwards et al., "Exendin-4 Reduces Fasting and Postprandial Glucose and Decreases Energy Intatke in Healthy Volunteers", American Journal of Physiology Encodcrinology and Metabolism, 2001, vol. 281, pp. E155-E161.
Flint et al., Glucagon-Like Peptide 1 Promotes Satiety and Suppresses Energy Intake in Humans, Journal of Clinical Investigation, 1998, vol. 101, No. 3, pp. 515-520.
Gothelf et al., "Weight Gain Associated With Increased Food Intake and Low Habitual Activity Levels in Male Adolescent Schizophrenic Inpatients Treated With Olanzapine", American Journal of Psychiatry, 2002, vol. 159, No. 6, pp. 1055-1057.
Hassan et al., "In Vivo Dynamic Distribution of 131I-Glucagon-Like Peptide-1 (7-36) Amide in the Rat Studied by Gamma Camera", Nuclear Medicine & Biology, 1999, vol. 26, pp. 413-420.

(Continued)

*Primary Examiner* — Gyan Chandra
(74) *Attorney, Agent, or Firm* — Leon Y. Lum

(57) ABSTRACT

The present invention describes administering a GLP-1 agonist to treat obesity caused by the administration of an obesity-inducing drug.

14 Claims, No Drawings

(56) References Cited

OTHER PUBLICATIONS

Jensen et al., "Transplantable Rat Glucagonomas Cause Acute Onset of Severe Anorexia and Adipsia Despite Highly Elevated NPY mRNA Levels in the Hypothalamic Arcuate Nucleus", Journal of Clinical Investigation, 1998, vol. 101, No. 2, pp. 503-510.
Jandacek et al., "Pharmaceutical Approaches to the Treatment of Obesity", Drug Discovery Today, 2004, vol. 9, No. 20, pp. 874-880.
Bernstein, "Induction of Obesity by Psychotropic Drugs", Annals of the New York Academy of Sciences, 1987, vol. 499, pp. 203-215.
Kieffer et al., "The Glucagon-Like Peptides", Endocrine Reviews, 1999, vol. 20, No. 6, pp. 876-913.
Kinzig et al., "The Diverse Roles of Specific GLP-1 Receptors in the Control of Food Intake and the Response to Visceral Illness", Journal of Neuroscience, 2002, vol. 22, No. 23, pp. 10470-10476.
Lykkegaard et al., "The Once-Daily Human GLP-1 Analog, Liraglutide, Reduces Olanzapine-Induced Weight Gain and Glucose Intolerance", Schizophrenia Research, 2008, vol. 103, pp. 94-103.
Leadbetter et al., "Clozapine-Induced Weight Gain: Prevalence and Clinical Relevance", American Journal of Psychiatry, 1992, vol. 149, pp. 68-72.
Li et al., "Olanzapine and Risperidone Disrupt Conditioned Avoidance Responding in Phencyclidine-Pretreated or Amphetamine-Pretreated Rats by Selectively Weakening Motivational Salience of Conditioned Stimulus", Behavior Pharmacology, 2009, vol. 20, No. 1, pp. 84-89.
Meeran et al., "Repeated Intracerebroventricular Administration of Glucagon-Like Peptide-1-(7-36) Amide or Exendin-(9-39) Alters Body Weight in the Rat", Endocrinology, 1999, vol. 140, No. 1, pp. 244-250.
McMahon et al., "PVN Infusion of GLP-1-(7-36) Amide Suppresses Feeding But Does Not Induce Aversion or Alter Locomotion in Rats", American Journal of Physiology, 1998, vol. 274, pp. R23-R29.
McIntyre et al., "Mechanisms of Antipsychotic-Induced Weight Gain", Journal of Clinical Psychiatry, 2001, vol. 62, No. 23, pp. 23-29.
Nauck et al., "Normalization of Fasting Hyperglycaemia by Exogenous Glucagon-Like Peptide 1(7-36 Amide) in Type 2 (Non-Insulin-Dependent) Diabetic Patients", Diabetologia, 1993, vol. 36, p. 741-744.
Procyshyn et al., "Clozapine's Effects on Body Weight and Resting Metabolic Rate: A Case Series", Schizophrenia Research, 2004, vol. 66, No. 2-3, pp. 159-162.
Sentissi et al., "Impact of Antipsychotic Treatments on the Movitation to Eat: Preliminary Results in 153 Schizophrenic Patients", Int. Clin. Psychopharmacol., 2009, vol. 24, No. 5, pp. 257-264.
Tang-Christensen et al., "Glucagon-Like Peptide 1(7-36) Amide's Central Inhibition of Feeding and Peripheral Inhibition of Drinking Are Abolished by Neonatal Monosodium Glutamate Treatment", Diabetes, 1998, vol. 47, pp. 530-537.
Turton et al, "A Role for Glucagon-Like Peptide-1 in the Central Regulation of Feeding", Nature, 1996, Vol. 379, pp. 69-72.
Van Dijk et al., "Glucagon-Like Peptide-1 (7-36) Amide: A Central Regulator of Satiety and Interoceptive Stress", Neuropeptides, 1999, vol. 33, No. 3, pp. 406-414.
Wettergren et al., "Glucagon-Like Peptide-1 Inhbiits Gastropancreatic Function by Inhibiting Central Parasympathetic Outflow", American Journal of Physiology, 1998, vol. 275, pp. 984-992.
Whitcomb et al., "Characterization of Saturable Binding Sites for Circulating Pancreatic Polypeptide in Rat Brain", American Journal of Physiology, 1990, vol. 259, pp. G687-G691.
Zander et al, "Effect of 6-Week Course of Glucagon-Like Peptide 1 on Glycaemic Control, Insulin Sensitivity, and Beta-Cell Function in Type 2 Diabetes: A Parallel-Group Study", Lancet, 2002, vol. 359, pp. 824-830.
Bays, "Current and Investigational Antiobesity Agents and Obesity Therapeutic Treatment Targets", Obesity Research, Aug. 8, 2004, vol. 12, No. 8, pp. 1197-1211.
Newcomer, JW. "Abnormalities of glucose metabolism associated with atypical antipsychotic drugs" Journal of Clinical Psychiatry vol. 65: 36-46 (2004).
Baptista, T et al. "Drug induced weight gain, an impediment to successful pharmacotherapy: focus on antipsychotics." Current Drug Targets. vol. 5(3): 279-299 (2004).
Newcomer, JW. "Second-generation (atypical) antipsychotics and metabolic effects—A comprehensive literature-review" CNS Drugs, vol. 19: 1-93 (2005).
Evans, S et al. "Nutritional Intervention to Prevent Weight Gain in Patients Commenced on Olanzapine: a Randomized Controlled Trial." Australian and New Zealand Journal of Psych vol. 39: 479-486 (2005).

\* cited by examiner

SEQUENCE LISTING

<160> NUMBER OF SEQ ID NOS: 3

<210> SEQ ID NO 1

```
-continued

<211> LENGTH: 31
<212> TYPE: PRT
<213> ORGANISM: Heloderma suspectum
<220> FEATURE:
<221> NAME/KEY: MISC_FEATURE
<222> LOCATION: (31)..(31)
<223> OTHER INFORMATION: X = P OR Y

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa
            20                  25                  30

<210> SEQ ID NO 2
<211> LENGTH: 40
<212> TYPE: PRT
<213> ORGANISM: Heloderma suspectum
<220> FEATURE:
<221> NAME/KEY: MISC_FEATURE
<222> LOCATION: (2)..(2)
<223> OTHER INFORMATION: WHEREIN X = S (EXENDIN-3) OR G (EXENDIN-4)
<220> FEATURE:
<221> NAME/KEY: MISC_FEATURE
<222> LOCATION: (3)..(3)
<223> OTHER INFORMATION: WHEREIN X = D (EXENDIN-3) OR E (EXENDIN-4)

<400> SEQUENCE: 2

His Xaa Xaa Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
        35                  40

<210> SEQ ID NO 3
<211> LENGTH: 44
<212> TYPE: PRT
<213> ORGANISM: Artificial Sequence
<220> FEATURE:
<223> OTHER INFORMATION: SYNTHETIC

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40
```

METHODS OF TREATING STEROID-INDUCED OBESITY USING GLP-1 AGONISTS

CROSS REFERENCE TO RELATED APPLICATIONS

This application is a continuation of U.S. application Ser. No. 11/629,238, filed Oct. 3, 2008, which is a 35 U.S.C. §371 National Stage application of PCT/EP2005/052475 filed May 31, 2005 which claimed priority of Danish Patent application PA 2004 00911 filed Jun. 11, 2004; this application claims priority under 35 U.S.C. §119(e) of U.S. Provisional application 60/628,418 filed Nov. 16, 2004.

FIELD OF THE INVENTION

The present invention relates to the use of GLP-1 agonists to regulate the weight of a patient, on or about to begin therapy with an obesity-inducing drug.

BACKGROUND OF THE INVENTION

Several drugs, particularly antipsychotics and certain steroids, are known to induce severe weight gain. A weight gain of about 7% over ideal body weight is considered a significant health risk due to the accompanying obesity that might lead to diabetes and cardiovascular diseases as well as a multitude of other obesity related diseases including cancer. With the average weight and BMI rapidly increasing over the whole world, the problem becomes even more severe.

The so-called atypical antipsychotic drugs are increasingly used to treat severe psychiatric diseases, among those, schizophrenia, schizotypal disorders, schizoaffective disorders, affective disorders, delusional disorders, and psychosis caused by use of psychoactive substances. Atypical antipsychotics include amisulpride, sulpiride, clozapine, risperidone, olanzapine, quetiapine, ziprasidone, and aripiprazole. Typical antipsychotics include chlorpromazine, perpherazine, thifluoperazine, thiothixene, haloperidol, and fluphenzine. Atypical antipsychotics are less likely to cause extrapyramidal side effects than the typical antipsychotics. In addition, atypical antipsychotics work on the negative symptoms and cognitive disturbances as well, which the typical antipsychotics generally do not.

Among the side effects of the atypical antipsychotics is weight gain, which in some cases is very pronounced. Clozapine and olanzapine are, especially, known to cause severe weight gain. The weight gain is an important side effect since it lowers patient compliance. Furthermore, patients with weight gain are at increased risk to develop diabetes, and a weight gain in this population would probably lead to even more cases of diabetes compared with the background population. Also, the typical antipsychotics and other CNS-active drugs such as lithium, mirtazapine, tri- and tetracyclic antidepressants, and valproat can cause weight gain.

It is not known exactly what causes the weight gain, but increased appetite as well as decreased metabolic rate are believed to be involved. Currently only very few drugs are on the market for controlling appetite and none with the primary mechanism of increasing or maintaining metabolic rate. The one appetite reducing drug on the market, sibutramine, acts in the CNS by modulating the serotonin neurotransmitter levels, and is considered contraindicated in patients with current or previous psychiatric disease.

GLP-1 has been described as an incretin hormone with a large array of effects. GLP-1 was discovered in 1984 and found to be an important incretin [Nauck, M. A.; Kleine, N.; Orskov, C.; Holst, J. J.; Willms, B.; Creutzfeldt, W., *Diabetologia* 1993, 36, 741-744]. It is released from the L-cells in the intestine upon a meal and potently releases insulin from the beta-cells in the pancreas. Numerous effects other than just stimulation of insulin release have been ascribed to GLP-1. In the pancreas, GLP-1 not only releases insulin, it does so in a glucose-dependent manner, and it has a number of other functionally important effects: stimulation of insulin biosynthesis, restoration of glucose sensitivity to the islets, and, stimulation of increased expression of the glucose transporter GLUT-2 and glucokinase. GLP-1 also has a number of effects on regulation of beta-cell mass, stimulation of replication and growth of existing beta-cells, inhibition of apoptosis, and neogenesis of new beta-cells from duct precursor cells, which leads to reduced hepatic glucose output. In the gut, GLP-1 is a potent inhibitor of motility and gastric emptying and has also been shown to inhibit gastric acid secretion. The inhibition of gastric emptying leads to decreased food intake and reduced body weight [Flint, A.; Raben, A.; Astrup, A.; Holst, J. J., *J Clin Inv* 1998, 101, 515-520; Zander, M.; Madsbad, S.; Madsen, J. L.; Holst, J. J., Lancet 2002, 359, 824-830]. Thus, the current belief is that the GLP-1 agonists may be able to control the progression of the type 2 diabetes disease by not only controlling blood glucose, but also by a number of other effects. GLP-1 has also been proposed to have direct effects on glucose uptake in liver, muscle, and adipose tissue, but the quantitative significance of these effects has been questioned [Kieffer, T. J.; Habener, J. F., *Endocrine Reviews* 1999, 20, 876-913]. New publications even suggest that it does not stop here, there may be specific receptors in the heart which along with the benefits of reducing blood glucose may protect from cardiovascular complications, and that GLP-1 stimulates memory and learning capabilities. A comprehensive review exists on the glucagon-like peptides [Kieffer, T. J.; Habener, J. F., *Endocrine Reviews* 1999, 20, 876-9139.

A large number of articles have been published on the effects of GLP-1 on food intake. GLP-1 reduces food intake, both after central administration and after peripheral administration (Turton, Nature 196:379;69-72, Flint *J Clin Inv* 1998, 101, 515-520). Also, central administration of high doses of GLP-1 induces taste aversion (Tang-Christensen, Diabetes 1998:47:530-537). However, site directed micro injections of GLP-1 into the PVN induces pharmacologically specific inhibition of feeding without induction of taste aversive behaviour (McMahon, Wellman, Am.J.Phys 1998:274, R23-R29). In animals having their arcuate nucleus lesioned by neonatal monosodium glutamate treatment, central administration of GLP-1 has lost its anorectic potential but is still inducing taste aversion (Tang-Christensen, Diabetes 1998:47:530-537). Further support of dissociated specific satiety inducing central targets of GLP-1 and non-specific taste aversion inducing central targets come from lesion studies showing that PVN constitute a target where GLP-1 elicits satiety whereas the central amygdala and the parabrachial nuclei constitute areas involved in mediating GLP-1 induced taste aversion (van Dijk and Thiele, Neuropeptides 1999: 33, 406-414). Other studies have confirmed that there are diverse roles of GLP-1 receptors in the control of food intake and taste aversion (Kinzig, J Neuroscience 2002:22(23): 10470-10476). Also, chronic repetitive central administration of the GLP-1 antagonist, exendin-9-39, enhances food intake suggesting that an endogenous tone of satiety mediating GLP-1 exists in central pathways mediating body weight homeostasis (Meeran, Endocrinology 199:140:244-250). In a human study, continuous infusion of GLP-1 to type 2 diabetic patients gave rise to marked improvement of glycaemic control and caused moderate yet non-significant weight loss (Zander, Lancet 2002: 359, 824-830). The site of the anorectic action of peripherally administered GLP-1 is unknown but participation of both central and peripheral sites in GLP-1 are likely, because a recent study has shown that radio labelled GLP-1 readily gains access to the central nervous system (Hassan, Nucl Med Biol 1999:26:413-420). The nucleus of the solitary tract is situated adjacent to the blood brain barrier free area postrema, and other studies using radio-labelled neuropeptides have shown that peripheral administration of neuropeptides gain access both to the area postrema as well as the adjacent subpostreme regions including the dorsal vagal complex (Whitcomb Am J Phys1990: 259:G687-G691). Thus, it is likely that peripherally administered GLP-1 enters the nucleus of the solitary tract with resulting impact on ascending neurones involved in regulation of food intake. Interaction of GLP-1 with vagal afferents from the gastrointestional tract should also be considered as mediator of its anorectic actions because transection of the vagus nerve renders the stomach of anaesthetised pigs insensitive to the akinetic actions of intravenously administered GLP-1 (Wettergren, Am J Phys 1998:275:984-992). Probably both vagal afferents and GLP-1 receptors accessible from the periphery are responsible for the anorexia induced by GLP-1, because we have seen that bilateral subdiaphragmatic vagotomy on rats carrying the anorectic GLP-1 producing tumour has no impact on the development of anorexia (Jensen, JCI 1998: 101:503-510). Last, GLP-1 has been shown to inhibit intake of different kinds of food, both rich in fat and in carbohydrate (Bjenning, Diabetes Res and Clin Prac 2000:50(1):S386).

Despite this in-depth knowledge it has never been described that a GLP-1 agonist could be used to treat drug-induced obesity.

SUMMARY OF THE INVENTION

In an aspect, the present invention relates to a method of treating obesity induced by antipsychotics or steroids by administering to a subject in need thereof a GLP-1 agonist, wherein the agonist is expected to regulate weight by decreasing appetite, increasing or maintaining metabolic rate, or a combination thereof.

Definitions

In the present context, "obese" or "obesity" implies an excess of adipose tissue. In this context obesity is preferably viewed as any degree of excess adiposity that imparts a health risk. The distinction between normal and obese individuals can only be approximated, but the health risk imparted by obesity is probably a continuum with increasing adiposity. However, in the context of the present invention, individuals with a body mass index (BMI=body weight in kilograms divided by the square of the height in meters) 25 or above are to be regarded as obese.

In the present context, "drug-induced obesity" is intended to indicate a weight gain resulting from a drug regimen wherein the subject taking the drug is considered obese or will be expected to become obese if the drug regimen is continued.

An "effective amount" of a compound as used herein means an amount sufficient to cure, alleviate, or partially arrest the clinical manifestations of a given disease or state and its complications. An amount adequate to accomplish this is defined as "effective amount." Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications; to delay the progression of the disease, disorder, or condition; to alleviate or relieve the symptoms and complications; and/or, to cure or eliminate the disease, disorder, or condition as well as to prevent the condition. Prevention is to be understood as the management and care of a patient for the purpose of combating the disease, condition, or disorder and includes the administration of the active compounds to prevent the onset of the symptoms or complications.

In the present context, "decreasing appetite" is intended to indicate that the amount of food (measured by its energy content) eaten by a group consisting of one or more subjects being administered a GLP-1 agonist and an obesity-causing drug is reduced compared to a similar control group not being administered a GLP-1 agonist, as provided in the present invention. Alternatively, "decreasing appetite" is intended to indicate that the amount of food (measured by its energy content) eaten by a subject being administered a GLP-1 agonist is reduced by at least 1, 2, 3, 4, 5, 6, 7, 8, 9, 10, 11, 12, 13, 14, 15, 16, 17, 18, 19, to 20% compared to food intake prior to administration of the GLP-1 agonist.

In the present context, "increasing or maintaining metabolic rate" is intended to indicate that the metabolic rate of a group consisting of one or more subjects being administered a GLP-1 agonist and an obesity-inducing drug is the same or greater than the metabolic rate of a similar control not group being administered the obesity-inducing drug or the GLP-1 agonist, as provided in the present invention. Alternatively, "increasing or maintaining metabolic rate" is intended to indicate that the metabolic rate of the subject being administered a drug regiment known or expected to cause obesity and a GLP-1 agonist is the same or greater than the metabolic rate prior to initiation of the obesity-inducing drug regimen and GLP-1 agonist administration.

In the present context, "subject" is intended to indicate a human that is currently on or about to begin a drug regimen that is known or expected to cause obesity.

In the present context, "drug regimen" is intended to mean the administration of a drug within its prescribed parameters of timing (e.g., once daily, twice daily, once weekly, etc.) and amount.

DESCRIPTION OF THE INVENTION

The present invention relates to the use of GLP-1 agonists to regulate the weight of a subject who is on or about to begin a drug regimen that has caused or is expected to cause a weight gain above ideal. The GLP-1 agonist is expected to regulate the subject's weight by decreasing appetite, increasing or maintaining metabolic rate, or a combination thereof.

In one embodiment, the invention provides a method of treating drug-induced obesity, comprising: administering to a subject in need thereof a therapeutically effective amount of a GLP-1 agonist, wherein the drug-induced obesity is induced by administration of an antipsychotic or a steroid.

In another embodiment, the invention provides a method for treating drug-induced obesity, wherein the obesity is caused by the administration of a steroid.

In another embodiment, the invention provides a method for treating drug-induced obesity, wherein the obesity is caused by the administration of an antipsychotic.

In another embodiment, the invention provides a method for treating drug-induced obesity, wherein antipsychotic is an atypical antipsychotic.

In another embodiment, the invention provides a method for treating drug-induced obesity, wherein the atypical antipsychotic is selected from amisulpride, sulpiride, clozapine, risperidone, olanzapine, quetiapine, ziprasidone, and aripiprazole.

In another embodiment, the invention provides a method for treating drug-induced obesity, wherein the atypical antipsychotic is clozapine.

In another embodiment, the invention provides a method for treating drug-induced obesity, wherein the atypical antipsychotic is olanzapine.

As noted above, obesity is preferably defined in terms of BMI. Thus, in another embodiment, the invention provides a method for treating drug-induced obesity, wherein the subject has a BMI of at least 25, 26, 27, 28, 29, or 30, preferably at least 25, more preferably at least 27, and even more preferably at least 30.

One important factor in maintaining an obesity-inducing drug regimen is slowing, stopping, or even reversing the weight gain caused by the regimen. Thus, in another embodiment, the present invention provides a method for treating obesity, wherein the subject's weight is about 7% over ideal. The faster the drug regimen causes weight gain, the less likely a subject will maintain the therapy and/or the greater the risk the subject is for developing secondary health conditions. Thus, in another embodiment, the present invention provides a method for treating obesity wherein in the past 1, 2, 3, 4, 5, 6, 7, 8, 9, 10, 11, or 12 months of obesity-inducing drug treatment, the subject has gained about 1, 2, 3, 4, 5, 6, 7, 8, 9, 10% or more body weight. In a further embodiment, the present invention provides a method for treating obesity wherein the weight gain resulted within the past twelve months of the drug regimen, has gained about 7% body weight. In another further embodiment, the present invention provides a method for treating obesity wherein the weight gain resulted within the past six months of the drug regimen, has gained about 7% body weight.

It could be helpful to administer a GLP-1 agonist prior to any sign of obesity or even weight gain. This could allow a patient to begin or maintain a drug regimen without having to bear the negative social or health consequences of undesired weight gain. Thus, in another embodiment of the present invention a method for treating obesity is provided wherein the GLP-1 agonist is administered to the subject prior to the onset of obesity. In still another embodiment of the present invention a method for treating obesity is provided wherein the GLP-1 agonist is administered at the start of the subject's obesity-inducing drug therapy. "At the start," as used herein, is intended to mean that the GLP-1 agonist therapy is begun on the same day; within a few days before or after; within a 1, 2, or 3 weeks before or after, or within 1, 2, or 3 months before or after the start of the obesity-inducing drug regimen.

In one embodiment of the methods of the present invention, the GLP-1 agonist is administered to the subject in connection with a meal. In the present context, "in connection with a meal" is intended to indicate a period of up to four hours before or after the meal, such as up to 3 hours before or after, such as up to 2 hours before or after, such as up to 1 hour before or after, such as 30 minutes before or after, such as 15 minutes before or after, such directly in connection with the meal. In a preferred embodiment, the GLP-1 agonist is administered concurrently with a daily dosage of obesity-inducing drug (or at least one of the daily dosages if either the obesity inducing drug or GLP-1 agonist are administered a different number of times per day). In two other preferred embodiments, the GLP-1 agonist can be administered prior to a daily dosage of obesity-inducing drug or after a daily dosage of obesity-inducing drug.

In the present context, "a GLP-1 agonist" is understood to refer to any compound, including peptides and non-peptide compounds, which fully or partially activate the human GLP-1 receptor. In a preferred embodiment, the "GLP-1 agonist" is any peptide or non-peptide small molecule that binds to a GLP-1 receptor, preferably with an affinity constant ($K_D$) or a potency ($EC_{50}$) of below 1 µM, e.g. below 100 nM as measured by methods known in the art (see e.g., WO 98/08871) and exhibits insulinotropic activity, where insulinotropic activity may be measured by in vivo or in vitro assays known to those of ordinary skill in the art. For example, the GLP-1 agonist may be administered to a subject and the insulin concentration measured over time.

In one embodiment, the GLP-1 agonist is selected from the group consisting of GLP-1(7-36)-amide, GLP-1(7-37), a GLP-1(7-36)-amide analogue, a GLP-1(7-37) analogue, or a derivative of any of these.

In the present application, the designation "an analogue" is used to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either at the N-terminal end or at the C-terminal end of the parent peptide or both. Amino acid residues may be naturally occurring amino acid residues or "non-natural" amino acid residues such as Aib or D-Alanine. Typically "an analogue" is a peptide wherein 6 or less amino acids have been substituted and/or added and/or deleted from the parent peptide, more preferably a peptide wherein 3 or less amino acids have been substituted and/or added and/or deleted from the parent peptide, and most preferably, a peptide wherein one amino acid has been substituted and/or added and/or deleted from the parent peptide.

In the present application, "a derivative" is used to designate a peptide or analogue thereof which is chemically modified by introducing e.g., ester, alkyl, or lipophilic functionalities on one or more amino acid residues of the peptide or analogue thereof. Other derivatives are PEGylated GLP-1 or dendrimeric GLP-1.

Methods for identifying GLP-1 agonists are described in WO 93/19175 (Novo Nordisk A/S) and examples of suitable GLP-1 analogues and derivatives which can be used according to the present invention includes those referred to in WO 99/43705 (Novo Nordisk A/S), WO 99/43706 (Novo Nordisk A/S), WO 99/43707 (Novo Nordisk A/S), WO 98/08871 (Novo Nordisk A/S), WO 99/43708 (Novo Nordisk A/S), WO 99/43341 (Novo Nordisk A/S), WO 87/06941 (The General Hospital Corporation), WO 90/11296 (The General Hospital Corporation), WO 91/11457 (Buckley et al.), WO 98/43658 (Eli Lilly & Co.), EP 0708179-A2 (Eli Lilly & Co.), EP 0699686-A2 (Eli Lilly & Co.), and WO 01/98331 (Eli Lilly & Co).

In one embodiment, the GLP-1 agonist is a derivative of GLP-1(7-36)-amide, GLP-1(7-37), a GLP-1(7-36)-amide analogue or a GLP-1(7-37) analogue, which comprises a lipophilic substituent. In this embodiment of the invention, the GLP-1 derivative preferably has three lipophilic substituents, more preferably two lipophilic substituents, and most preferably one lipophilic substituent attached to the parent peptide (e.g., GLP-1(7-36)-amide, GLP-1(7-37), a GLP-1(7-36)-amide analogue or a GLP-1(7-37) analogue), where each lipophilic substituent(s) preferably has 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, to 40 carbon atoms, more preferably 8-30 carbon atoms, even more preferably 8-25 carbon atoms, even more preferably 12-25 carbon atoms, and most preferably 14-18 carbon atoms.

In one embodiment, the lipophilic substituent comprises a partially or completely hydrogenated cyclopentanophenathrene skeleton. In another embodiment, the lipophilic substituent is a straight-chain or branched alkyl group. In yet another embodiment, the lipophilic substituent is an acyl group of a straight-chain or branched fatty acid. Preferably, the lipophilic substituent is an acyl group having the formula $CH_3(CH_2)_nCO—$, wherein n is an integer from 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, to 38, preferably an integer from 12 to 38, and most preferably is selected from $CH_3(CH_2)_{12}CO—$, $CH_3(CH_2)_{14}CO—$, $CH_3(CH_2)_{16}CO—$, $CH_3(CH_2)_{18}CO—$, $CH_3(CH_2)_{20}CO—$ and $CH_3(CH_2)_{22}CO—$. In a more preferred embodiment, the lipophilic substituent is tetradecanoyl. In a most preferred embodiment, the lipophilic substituent is hexadecanoyl.

In a further embodiment of the present invention, the lipophilic substituent has a group which is negatively charged such as a carboxylic acid group. For example, the lipophilic substituent may be an acyl group of a straight-chain or branched alkane $\alpha,\omega$-dicarboxylic acid of the formula $HOOC(CH_2)_mCO—$, wherein m is an integer from 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, to 38, preferably an integer from 12 to 38, and most preferably is selected from $HOOC(CH_2)_{14}CO—$, $HOOC(CH_2)_{16}CO—$, $HOOC(CH_2)_{18}CO—$, $HOOC(CH_2)_{20}CO—$, or $HOOC(CH_2)_{22}CO—$.

In the GLP-1 derivatives of the invention, the lipophilic substituent(s) contain a functional group which can be attached to one of the following functional groups of an amino acid of the parent GLP-1 peptide:

(a) the amino group attached to the alpha-carbon of the N-terminal amino acid, (b) the carboxy group attached to the alpha-carbon of the C-terminal amino acid, (c) the epsilon-amino group of any Lys residue, (d) the carboxy group of the R group of any Asp and Glu residue, (e) the hydroxy group of the R group of any Tyr, Ser and Thr residue, (f) the amino group of the R group of any Trp, Asn, Gln, Arg, and His residue, or (g) the thiol group of the R group of any Cys residue.

In one embodiment, a lipophilic substituent is attached to the carboxy group of the R group of any Asp and Glu residue. In another embodiment, a lipophilic substituent is attached to the carboxy group attached to the alpha-carbon of the C-terminal amino acid. In a preferred embodiment, a lipophilic substituent is attached to the epsilon-amino group of any Lys residue.

In another preferred embodiment of the invention, the lipophilic substituent is attached to the parent GLP-1 peptide by means of a spacer. A spacer must contain at least two functional groups, one to attach to a functional group of the lipophilic substituent and the other to a functional group of the parent GLP-1 peptide.

In one embodiment, the spacer is an amino acid residue except Cys or Met, or a dipeptide such as Gly-Lys. For purposes of the present invention, the phrase "a dipeptide such as Gly-Lys" means any combination of two amino acids except Cys or Met, preferably a dipeptide wherein the C-terminal amino acid residue is Lys, His, or Trp, preferably Lys, and the N-terminal amino acid residue is Ala, Arg, Asp, Asn, Gly, Glu, Gln, Ile, Leu, Val, Phe, Pro, Ser, Tyr, Thr, Lys, His, or Trp. Preferably, an amino group of the parent peptide forms an amide bond with a carboxylic group of the amino acid residue or dipeptide spacer, and an amino group of the amino acid residue or dipeptide spacer forms an amide bond with a carboxyl group of the lipophilic substituent.

Preferred spacers are lysyl, glutamyl, asparagyl, glycyl, beta-alanyl, and gamma-aminobutanoyl, each of which constitutes an individual embodiment. Most preferred spacers are glutamyl and beta-alanyl. When the spacer is Lys, Glu, or Asp, the carboxyl group thereof may form an amide bond with an amino group of the amino acid residue, and the amino group thereof may form an amide bond with a carboxyl group of the lipophilic substituent. When Lys is used as the spacer, a further spacer may in some instances be inserted between the $\epsilon$-amino group of Lys and the lipophilic substituent. In one embodiment, such a further spacer is succinic acid which forms an amide bond with the $\epsilon$-amino group of Lys and with an amino group present in the lipophilic substituent. In another embodiment such a further spacer is Glu or Asp which forms an amide bond with the $\epsilon$-amino group of Lys and another amide bond with a carboxyl group present in the lipophilic substituent, that is, the lipophilic substituent is a $N^\epsilon$-acylated lysine residue.

In another embodiment, the spacer is an unbranched alkane $\alpha,\omega$-dicarboxylic acid group having from 1 to 7 methylene groups, which spacer forms a bridge between an amino group of the parent peptide and an amino group of the lipophilic substituent. Preferably, the spacer is succinic acid.

In a further embodiment, the lipophilic substituent with the attached spacer is a group of the formula $CH_3(CH_2)_pNH-CO(CH_2)_qCO—$, wherein p is an integer from 8, 9, 10, 11, 12, 13, 14, 15, 16, 17, 18, 19, 20, 21, 22, 23, 24, 25, 26, 27, 28, 29, 30, 31, 32, to 33, preferably from 12 to 28 and q is an integer from 1 to 6, preferably 2.

In a further embodiment, the lipophilic substituent with the attached spacer is a group of the formula $CH_3(CH_2)_rCO-NHCH(COOH)(CH_2)_2CO—$, wherein r is an integer from 4, 5, 6, 7, 8, 9, 10, 11, 12, 13, 14, 15, 16, 17, 18, 19, 20, 21, 22, 23, to 24, preferably from 10 to 24.

In a further embodiment, the lipophilic substituent with the attached spacer is a group of the formula $CH_3(CH_2)_sCO—NHCH((CH_2)_2COOH)CO—$, wherein s is an integer from 4, 5, 6, 7, 8, 9, 10, 11, 12, 13, 14, 15, 16, 17, 18, 19, 20, 21, 22, 23, to 24, preferably from 10 to 24.

In a further embodiment, the lipophilic substituent is a group of the formula $COOH(CH_2)_tCO—$ wherein t is an integer from 6, 7, 8, 9, 10, 11, 12, 13, 14, 15, 16, 17, 18, 19, 20, 21, 22, 23, to 24.

In a further embodiment, the lipophilic substituent with the attached spacer is a group of the formula $—NHCH(COOH)(CH_2)_4NH—CO(CH_2)_uCH_3$, wherein u is an integer from 8, 9, 10, 11, 12, 13, 14, 15, 16, 17, to 18.

In a further embodiment, the lipophilic substituent with the attached spacer is a group of the formula $CH_3(CH_2)_vCO—NH—(CH_2)_z—CO$, wherein v is an integer from 4 to 24 and z is an integer from 1 to 6.

In a further embodiment, the lipophilic substituent with the attached spacer is a group of the formula —NHCH(COOH)(CH$_2$)$_4$NH—COCH((CH$_2$)$_2$COOH)NH—CO(CH$_2$)$_w$CH$_3$, wherein w is an integer from 10, 11, 12, 13, 14, 15, to 16.

In a further embodiment, the lipophilic substituent with the attached spacer is a group of the formula —NHCH(COOH)(CH$_2$)$_4$NH—CO(CH$_2$)$_2$CH(COOH)NHCO(CH$_2$)$_x$CH$_3$, wherein x is zero or an integer from 1, 2, 3, 4, 5, 6, 7, 8, 9, 10, 11, 12, 13, 14, 15, 16, 17, 18, 19, 20, 21, to 22, preferably 10 to 16.

In yet another embodiment the GLP-1 agonist is Arg$^{34}$, Lys$^{26}$(N$^\epsilon$-($\gamma$-Glu(N$^\alpha$-hexade-canoyl)))-GLP-1(7-37).

In yet another embodiment, the GLP-1 agonist is selected from the group consisting of Gly$^8$-GLP-1(7-36)-amide, Gly$^8$-GLP-1(7-37), Val$^8$-GLP-1(7-36)-amide, Val$^8$-GLP-1(7-37), Val$^8$Asp$^{22}$-GLP-1(7-36)-amide, Val$^8$Asp$^{22}$-GLP-1(7-37), Val$^8$Glu$^{22}$-GLP-1(7-36)-amide, Val$^8$Glu$^{22}$-GLP-1(7-37), Val$^8$Lys$^{22}$-GLP-1(7-36)-amide, Val$^8$Lys$^{22}$-GLP-1(7-37), Val$^8$Arg$^{22}$-GLP-1(7-36amide, Val$^8$Arg$^{22}$-GLP-1(7-37), Val$^8$His$^{22}$-GLP-1(7-36)-amide, Val$^8$His$^{22}$-GLP-1(7-37), analogues thereof, and derivatives of any of these.

In yet another embodiment, the GLP-1 agonist is selected from the group consisting of Arg$^{26}$-GLP-1(7-37); Arg$^{34}$-GLP-1(7-37); Lys$^{36}$-GLP-1(7-37); Arg$^{26,34}$Lys$^{36}$-GLP-1(7-37); Arg$^{26,34}$-GLP-1(7-37); Arg$^{26,34}$Lys$^{40}$-GLP-1(7-37); Arg$^{26}$Lys$^{36}$-GLP-1(7-37); Arg$^{34}$Lys$^{36}$-GLP-1(7-37); Val$^8$Arg$^{22}$-GLP-1(7-37); Met$^8$Arg$^{22}$-GLP-1(7-37); Gly$^8$His$^{22}$-GLP-1(7-37); Val$^8$His$^{22}$-GLP-1(7-37); Met$^8$His$^{22}$-GLP-1(7-37); His$^{37}$-GLP-1(7-37); Gly$^8$-GLP-1(7-37); Val$^8$-GLP-1(7-37); Met$^8$-GLP-1(7-37); Gly$^8$Asp$^{22}$-GLP-1(7-37); Val$^8$Asp$^{22}$-GLP-1(7-37); Met$^8$Asp$^{22}$-GLP-1(7-37); Gly$^8$Glu$^{22}$-GLP-1(7-37); Val$^8$Glu$^{22}$-GLP-1(7-37); Met$^8$Glu$^{22}$-GLP-1(7-37); Gly$^8$Lys$^{22}$-GLP-1(7-37); Val$^8$Lys$^{22}$-GLP-1(7-37); Met$^8$Lys$^{22}$-GLP-1(7-37); Gly$^8$Arg$^{22}$-GLP-1(7-37); Val$^8$Lys$^{22}$His$^{37}$-GLP-1(7-37); Gly$^8$Glu$^{22}$His$^{37}$-GLP-1(7-37); Val$^8$Glu$^{22}$His$^{37}$-GLP-1(7-37); Met$^8$Glu$^{22}$His$^{37}$-GLP-1(7-37); Gly$^8$Lys$^{22}$ His$^{37}$-GLP-1(7-37); Met$^8$Lys$^{22}$His$^{37}$-GLP-1(7-37); Gly$^8$Arg$^{22}$His$^{37}$-GLP-1(7-37); Val$^8$Arg$^{22}$His$^{37}$-GLP-1(7-37); Met$^8$Arg$^{22}$His$^{37}$-GLP-1(7-37); Gly$^8$His$^{22}$His$^{37}$-GLP-1(7-37); Val$^8$His$^{22}$His$^{37}$-GLP-1(7-37); Met$^8$His$^{22}$His$^{37}$-GLP-1(7-37); Gly$^8$His$^{37}$-GLP-1(7-37); Val$^8$His$^{37}$-GLP-1(7-37); Met$^8$His$^{37}$-GLP-1(7-37); Gly$^8$Asp$^{22}$ His$^{37}$-GLP-1(7-37); Val$^8$Asp$^{22}$His$^{37}$-GLP-1(7-37); Met$^8$Asp$^{22}$His$^{37}$-GLP-1(7-37); Arg$^{26}$-GLP-1(7-36)-amide; Arg$^{34}$-GLP-1(7-36)-amide; Lys$^{36}$-GLP-1(7-36)-amide; Arg$^{26,34}$Lys$^{36}$-GLP-1(7-36)-amide; Arg$^{26,34}$-GLP-1(7-36)-amide; Arg$^{26,34}$Lys$^{40}$-GLP-1(7-36)-amide; Arg$^{26}$Lys$^{36}$-GLP-1(7-36)-amide; Arg$^{34}$Lys$^{36}$-GLP-1(7-36)-amide; Gly$^8$-GLP-1(7-36)-amide; Val$^8$-GLP-1(7-36)-amide; Met$^8$-GLP-1(7-36)-amide; Gly$^8$Asp$^{22}$-GLP-1(7-36)-amide; Gly$^8$Glu$^{22}$His$^{37}$-GLP-1(7-36)-amide; Val$^8$Asp$^{22}$-GLP-1(7-36)-amide; Met$^8$Asp$^{22}$-GLP-1(7-36)-amide; Gly$^8$Glu$^{22}$-GLP-1(7-36)-amide; Val$^8$Glu$^{22}$-GLP-1(7-36)-amide; Met$^8$Glu$^{22}$-GLP-1(7-36)-amide; Gly$^8$Lys$^{22}$-GLP-1(7-36)-amide; Val$^8$Lys$^{22}$-GLP-1(7-36)-amide; Met$^8$Lys$^{22}$-GLP-1(7-36)-amide; Gly$^8$His$^{22}$His$^{37}$-GLP-1(7-36)-amide; Gly$^8$Arg$^{22}$-GLP-1(7-36)-amide; Val$^8$Arg$^{22}$-GLP-1(7-36)-amide; Met$^8$Arg$^{22}$-GLP-1(7-36)-amide; Gly$^8$His$^{22}$-GLP-1(7-36)-amide; Val$^8$His$^{22}$-GLP-1(7-36)-amide; Met$^8$His$^{22}$-GLP-1(7-36)-amide; His$^{37}$-GLP-1(7-36)-amide; Val$^8$Arg$^{22}$His$^{37}$-GLP-1(7-36)-amide; Met$^8$Arg$^{22}$His$^{37}$-GLP-1(7-36)-amide; Gly$^8$His$^{37}$-GLP-1(7-36)-amide; Val$^8$His$^{37}$-GLP-1(7-36)-amide; Met$^8$His$^{37}$-GLP-1(7-36)-amide; Gly$^8$Asp$^{22}$ His$^{37}$-GLP-1(7-36)-amide; Val$^8$Asp$^{22}$His$^{37}$-GLP-1(7-36)-amide; Met$^8$Asp$^{22}$His$^{37}$-GLP-1(7-36)-amide; Val$^8$Glu$^{22}$His$^{37}$-GLP-1(7-36)-amide; Met$^8$Glu$^{22}$His$^{37}$-GLP-1(7-36)-amide; Gly$^8$Lys$^{22}$ His$^{37}$-GLP-1(7-36)-amide; Val$^8$Lys$^{22}$His$^{37}$-GLP-1(7-36)-amide; Met$^8$Lys$^{22}$His$^{37}$-GLP-1(7-36)-amide; Gly$^8$Arg$^{22}$His$^{37}$-GLP-1(7-36)-amide; Val$^8$His$^{22}$His$^{37}$-GLP-1(7-36)-amide; Met$^8$His$^{22}$His$^{37}$-GLP-1(7-36)-amide; and derivatives thereof.

In yet another embodiment the GLP-1 agonist is selected from the group consisting of Val$^8$Trp$^{19}$Glu$^{22}$-GLP-1(7-37), Val$^8$Glu$^{22}$Val$^{25}$-GLP-1(7-37), Val$^8$Tyr$^{16}$Glu$^{22}$-GLP-1(7-37), Val$^8$Trp$^{16}$Glu$^{22}$-GLP-1(7-37), Val$^8$Leu$^{16}$Glu$^{22}$-GLP-1(7-37), Val$^8$Tyr$^{18}$Glu$^{22}$-GLP-1(7-37), Val$^8$Glu$^{22}$His$^{37}$-GLP-1(7-37), Val$^8$Glu$^{22}$Ile$^{33}$-GLP-1(7-37), Val$^8$Trp$^{16}$Glu$^{22}$Val$^{25}$Ile$^{33}$-GLP-1(7-37), Val$^8$Trp$^{16}$Glu$^{22}$Ile$^{33}$-GLP-1(7-37), Val$^8$Glu$^{22}$Val$^{25}$Ile$^{33}$-GLP-1(7-37), Val$^8$Trp$^{16}$Glu$^{22}$Val$^{25}$-GLP-1(7-37), analogues thereof, and derivatives of any of these.

In yet another embodiment the GLP-1 agonist is a stable GLP-1 analogue/-derivative. Throughout this application a "stable GLP-1 analogue/derivative" means a GLP-1 analogue or a derivative of a GLP-1 analogue which exhibits an in vivo plasma elimination half-life of at least 10 hours in man, as determined by the method described below. Examples of stable GLP-1 analogue/derivatives can be found in WO 98/08871 and WO 99/43706. The method for determination of plasma elimination half-life of a compound in man is: The compound is dissolved in an isotonic buffer, pH 7.4, PBS or any other suitable buffer. The dose is injected peripherally, preferably in the abdominal or upper thigh. Blood samples for determination of active compound are taken at frequent intervals, and for a sufficient duration to cover the terminal elimination part (e.g., Pre-dose, 1, 2, 3, 4, 5, 6, 7, 8, 10, 12, 24 (day 2), 36 (day 2), 48 (day 3), 60 (day 3), 72 (day 4) and 84 (day 4) hours post dose). Determination of the concentration of active compound is performed as described in Wilken et al., Diabetologia 43(51):A143, 2000. Derived pharmacokinetic parameters are calculated from the concentration-time data for each individual subject by use of non-compartmental methods, using the commercially available software WinNonlin Version 2.1 (Pharsight, Cary, N.C., USA). The terminal elimination rate constant is estimated by log-linear regression on the terminal log-linear part of the concentration-time curve, and used for calculating the elimination half-life.

Stable GLP-1 analogues and derivatives are disclosed in WO 98/08871 (analogues with lipophilic substituent) and in WO 02/46227 (analogues fused to serum albumin or to Fc portion of an Ig).

In another embodiment, The GLP-1 agonist is formulated so as to have a half-life in man, as discussed above, of at least 10 hours. This may be obtained by sustained release formulations known in the art.

In yet another embodiment the GLP-1 agonist is exendin-4 or exendin-3, an exendin-4 or exendin-3 analogue, or a derivative of any of these.

Examples of exendins as well as analogues, derivatives, and fragments thereof to be included within the present invention are those disclosed in WO 97/46584, U.S. Pat. No. 5,424,286, and WO 01/04156. U.S. Pat. No. 5,424,286 describes a method for stimulating insulin release with an exendin polypeptide. The exendin polypeptides disclosed include HGEGTFTSDLSKQMEEEAVRLFIEWLKNGGX (SEQ ID NO:1); wherein X=P or Y, and HX1X2GTFITSDLSKQMEEEAVRLFIEWLKNGGPSSG APPPS (SEQ ID NO:2); wherein X1X2=SD (exendin-3) or GE (exendin-4)). WO 97/46584 describes truncated versions of exendin peptide(s). The disclosed peptides increase secretion and biosynthesis of insulin, but reduce those of glucagon. WO 01/04156 describes exendin-4 analogues and derivatives as well as the preparation of these molecules. Exendin-4 analogues stabilized by fusion to serum albumin or Fc portion of an Ig are disclosed in WO 02/46227.

In one embodiment, the exendin-4 analogue is HGEGT-FTSDLSKQMEEEAVRLFIEWLKNGGPSS-GAPPSKKKKKK (SEQ ID NO:3).

In yet another embodiment the GLP-1 agonist is a stable exendin-4 analogue/-derivative. The term "stable exendin-4 analogue/derivative", as used herein refers to an exendin-4(1-39) analogue or a derivative of an exendin-4(1-39) analogue which exhibits an in vivo plasma elimination half-life of at least 10 hours in man, as determined by the method described above for a "stable GLP-1 analogue/derivative".

In still another embodiment, the GLP-1 agonist is Aib$^{8,35}$ GLP-1(7-36) amide (Aib=α-amino isobutyric acid).

In still another embodiment, the GLP-1 agonist is Ser$^{38}$, Lys$^{39,40,41,42,43,44}$-Exendin-4(1-39)amide.

In still another embodiment the GLP-1 agonist is selected from the non-peptide small molecule GLP-1 agonists disclosed in WO 00/42026.

The present invention also encompasses pharmaceutically acceptable salts of the GLP-1 agonists. Such salts include pharmaceutically acceptable acid addition salts, pharmaceutically acceptable metal salts, ammonium, and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates which the present GLP-1 agonists are able to form.

Peptide GLP-1 compounds can be produced by appropriate derivatization of an appropriate peptide backbone which has been produced by recombinant DNA technology or by peptide synthesis (e.g., Merrifield-type solid phase synthesis) as known in the art of peptide synthesis and peptide chemistry.

The route of administration of GLP-1 agonists may be any route which effectively transports the active compound to the appropriate or desired site of action, such as oral, nasal, buccal, pulmonal, transdermal, or parenteral.

Medicaments or pharmaceutical compositions containing a GLP-1 agonist such as Arg$^{34}$, Lys$^{26}$(N$^\epsilon$-(γ-Glu(N$^\alpha$-hexadecanoyl)))-GLP-1(7-37) may be administered parenterally to a patient in need thereof. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of a GLP-1 agonist in the form of a nasal or pulmonal spray. As a still further option, the GLP-1 agonist can also be administered transdermally, e.g., from a patch, optionally an iontophoretic patch, or transmucosally, e.g., bucally. The abovementioned possible ways to administer GLP-1 agonists are not considered as limiting the scope of the invention.

In one embodiment, the dosage of GLP-1 agonist to be administered to a patient in a method of the invention is from about 0.1 ug/kg/day to about 40 ug/kg/day.

In another embodiment, the dosage of GLP-1 agonist to be administered to a patient in a method of the invention is from about 0.01 mg/day to about 5 mg/day.

In one embodiment, a GLP-1 agonist is co-administered together with a further therapeutically active compound used in the treatment of obesity or to induce weight loss or to maintain an obtained weight loss, or used in the treatment of diseases or states where obesity is part of the etiology. Examples of further therapeutically active compounds include anti-diabetic agents, antihyperlipidemic agents, anti-obesity agents, antihypertensive agents, and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines; sulfonyl-ureas; biguanides; meglitinides, oxadiazolidinediones; thiazolidinediones; insulin sensitizers; α-glucosidase inhibitors; agents acting on the ATP-dependent potassium channel of the pancreatic β-cells e.g. potassium channel openers such as those disclosed in WO 97/26265, WO 99/03861 and WO 00/37474 (Novo Nordisk A/S) which are incorporated herein by reference; potassium channel openers, such as ormitiglinide; potassium channel blockers such as nateglinide or BTS-67582; glucagon antagonists such as those disclosed in WO 99/01423 and WO 00/39088 (Novo Nordisk A/S and Agouron Pharmaceuticals, Inc.), all of which are incorporated herein by reference; GLP-1 agonists such as those disclosed in WO 00/42026 (Novo Nordisk A/S and Agouron Pharmaceuticals, Inc.), which are incorporated herein by reference; DPP-IV (dipeptidyl peptidase-IV) inhibitors; PTPase (protein tyrosine phosphatase) inhibitors; glucokinase activators, such as those described in WO 02/08209 to Hoffmann La Roche; inhibitors of hepatic enzymes involved in stimulation of gluconeogenesis and/or glycogenolysis; glucose intake modulators; GSK-3 (glycogen synthase kinase-3) inhibitors; compounds modifying the lipid metabolism such as antihyperlipidemic agents and antilipidemic agents; compounds lowering food intake; and, PPAR (peroxisome proliferator-activated receptor) and RXR (retinoid X receptor) agonists such as ALRT-268, LG-1268. or LG-1069.

Other examples of suitable additional therapeutically active compounds include insulin or insulin analogues, sulfonylurea e.g. tolbutamide, chlorpropamide, tolazamide, glibenclamide, glipizide, glimepiride, glicazide, glyburide, biguanide e.g. metformin, meglitinide e.g. repaglinide or senaglinide/nateglinide.

Other examples of suitable additional therapeutically active compounds include thiazolidinedione insulin sensitizer e.g. troglitazone, ciglitazone, pioglitazone, rosiglitazone, isaglitazone, darglitazone, englitazone, CS-011/CI-1037 or T 174 or the compounds disclosed in WO 97/41097 (DRF-2344), WO 97/41119, WO 97/41120, WO 00/41121 and WO 98/45292 (Dr. Reddy's Research Foundation), which are incorporated herein by reference.

Other examples of suitable additional therapeutically active compounds include insulin sensitizer e.g. such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313 (NN622/DRF-2725), WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

Other examples of suitable additional therapeutically active compounds include α-glucosidase inhibitor e.g. voglibose, emiglitate, miglitol or acarbose.

Other examples of suitable additional therapeutically active compounds include glycogen phosphorylase inhibitor e.g. the compounds described in WO 97/09040 (Novo Nordisk A/S).

Other examples of suitable additional therapeutically active compounds include a glucokinase activator.

Other examples of suitable additional therapeutically active compounds include an agent acting on the ATP-dependent potassium channel of the pancreatic β-cells e.g. tolbutamide, glibenclamide, glipizide, glicazide, BTS-67582 or repaglinide.

Other examples of suitable additional therapeutically active compounds include nateglinide.

Other examples of suitable additional therapeutically active compounds include an antihyperlipidemic agent or an antilipidemic agent e.g. cholestyramine; colestipol; clofibrate; gemfibrozil; lovastatin; pravastatin; simvastatin; probucol; or, dextrothyroxine.

Other examples of said additional therapeutically active compounds include anti-obesity compounds or appetite regulating agents. Such compounds may be selected from the group consisting of cannabinoid receptor antagonists (e.g. rimonabant), CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β33 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, chemical uncouplers, leptin agonists, DA (dopamine) agonists (bromocriptin, doprexin), lipase/amylase inhibitors, PPAR modulators, RXR modulators, TR β3 agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists and ciliary neurotrophic factor. Further antiobesity agents are bupropion (antidepressant), topiramate (anticonvulsant), ecopipam (dopamine D1/D5 antagonist), naltrexone (opioid antagonist), and peptide $YY_{3-36}$ (Batterham et al, Nature 418, 650-654 (2002)).

In one embodiment, the antiobesity agent is leptin.

In one embodiment, the antiobesity agent is peptide $YY_{3-36}$.

In one embodiment, the antiobesity agent is a serotonin and norepinephrine reuptake inhibitor e.g. sibutramine.

In one embodiment, the antiobesity agent is a lipase inhibitor e.g. orlistat.

In one embodiment, the antiobesity agent is an adrenergic CNS stimulating agent e.g., dexamphetamine, amphetamine, phentermine, mazindol phendimetrazine, diethylpropion, fenfluramine, or dexfenfluramine.

In one embodiment, the antiobesity agent is oxynthomodulin, as disclosed in WO 03/22304 (Imperial College).

In one embodiment, the antiobesity agent is a ghrelin antagoninst, e.g. as disclosed in WO 01/56592.

In one embodiment, the antiobesity agent is an energy expenditure modifier.

In one embodiment, the antiobesity agent is a 11β-Hydroxysteroid Dehydrogenase Type 1 Inhibitor.

Other examples of suitable additional therapeutically active compounds include antihypertensive agents. Examples of antihypertensive agents are β-blockers such as alprenolol, atenolol, timolol, pindolol, propranolol and metoprolol; ACE (angiotensin converting enzyme) inhibitors such as benazepril, captopril, enalapril, fosinopril, lisinopril, quinapril, and ramipril; calcium channel blockers such as nifedipine, felodipine, nicardipine, isradipine, nimodipine, diltiazem, and verapamil; and. α-blockers such as doxazosin, urapidil, prazosin, and terazosin.

Pharmaceutical Compositions

Pharmaceutical compositions containing GLP-1 agonists such as $Arg^{34}$, $Lys^{26}(N_\epsilon\text{-}(\gamma\text{-Glu}(N^\alpha\text{-hexadecanoyl})))\text{-GLP-1}$ (7-37) may be prepared by conventional techniques, e.g., as described in Remington's *Pharmaceutical Sciences*, 1985 or in Remington: *The Science and Practice of Pharmacy*, 19$^{th}$ edition, 1995.

Thus, injectable compositions of GLP-1 agonists can be prepared using the conventional techniques of the pharmaceutical industry which involves dissolving and mixing the ingredients as appropriate to give the desired end product.

For example, a GLP-1 agonist such as $Arg^{34}$, $Lys^{26}(N^\epsilon(\gamma\text{-Glu}(N^\alpha\text{-hexadecanoyl})))\text{-GLP-1}(7\text{-}37)$ may be dissolved in an amount of water which is somewhat less than the final volume of the composition to be prepared. An isotonicity agent, a preservative and a buffer are added as required and the pH value of the solution is adjusted—if necessary—using an acid, e.g., hydrochloric acid, or a base, e.g., aqueous sodium hydroxide as needed. Finally, the volume of the solution is adjusted with water to give the desired concentration of the ingredients.

In one embodiment of the invention, the formulation of the GLP-1 agonist has a pH in the range from 7.0 to 10. In another embodiment of the invention the formulation has a pH in the range from 7.0 to 9.5. In a further embodiment of the invention the formulation has a pH in the range from 7.0 to 8.5. In yet another embodiment of the invention the formulation has a pH in the range from 7.0 to 8.0, preferably from 7.4 to 7.8. In a further embodiment of the invention the formulation has a pH in the range from 9.0 to 10.

Examples of isotonic agents to be used in the formulations of the invention are those selected from the group consisting of a salt (e.g., sodium chloride), a polyhydric alcohol (e.g., xylitol, mannitol, sorbitol or glycerol), a monosaccharide (e.g., glucose or maltose), a disccharide (e.g., sucrose), an amino acid (e.g., L-glycine, L-histidine, arginine, lysine, isoleucine, aspartic acid, tryptophan, threonine), polyethyleneglycol (e.g., PEG400), prolpylene glycol, or mixtures thereof.

In a further embodiment of the invention the isotonic agent is selected from the group consisting of sodium chloride, glycerol, mannitol, glucose, sucrose, L-glycine, L-histidine, arginine, lysine or mixtures thereof. Each one of these specific isotonic agents constitutes an alternative embodiment of the invention.

Examples of preservatives to be used in the formulations of the invention are phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. Each one of these specific preservatives constitutes an alternative embodiment of the invention. In a preferred embodiment of the invention the preservative is phenol or m-cresol.

Examples of suitable buffers to be used in the formulations of the invention are sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, or mixtures thereof. Each one of these specific buffers constitutes an alternative embodiment of the invention. In a preferred embodiment of the invention the buffer is glycylglycine, sodium dihydrogen phosphate, disodium hydrogen phosphate, sodium phosphate or mixtures thereof.

Further to the above-mentioned components, solutions containing a GLP-1 agonist may also contain a surfactant in order to improve the solubility and/or the stability of the peptide. In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g., Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g., 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g., lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the postively charged DODAC, DOTMA, DCP, BISHOP, lysophosphatidylserine and lysophosphatidylthreonine, zwitterionic surfactants (e.g., N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g., cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g., sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment of the invention.

The use of isotonicity agents, preservatives, and surfactants are well known in the pharmaceutical arts and reference is made to Remington: *The Science and Practice of Pharmacy*, $19^{th}$ edition, 1995.

In a further embodiment of the invention the GLP-1 agonist is present in a formulation of the invention in a concentration from 0.1 mg/mL to 80 mg/mL. In a further embodiment of the invention the GLP-1 agonist is present in a concentration from 1 mg/mL to 80 mg/mL. In a further embodiment of the invention the GLP-1 agonist is present in a concentration from 0.1 mg/mL to 50 mg/mL. In a further embodiment of the invention the GLP-1 agonist is present in a concentration from 1 mg/mL to 50 mg/mL. In a further embodiment of the invention the GLP-1 agonist is present in a concentration from 0.1 mg/mL to 20 mg/mL. In a further embodiment of the invention the GLP-1 agonist is present in a concentration from 1 mg/mL to 20 mg/mL. In a further embodiment of the invention the GLP-1 agonist is present in a concentration from 0.1 mg/mL to 10 mg/mL. In a further embodiment of the invention the GLP-1 agonist is present in a concentration from 1 mg/mL to 10 mg/mL. In a further embodiment of the invention the GLP-1 agonist is present in a concentration from 0.1-5 mg/mL. In a further embodiment of the invention the GLP-1 agonist is present in a concentration from 1-5 mg/mL. In a further embodiment of the invention the GLP-1 agonist is present in a concentration from 0.1-0.5 mg/mL. In a further embodiment of the invention the GLP-1 agonist is present in a concentration from 0.6-1 mg/mL. Each one of these specific concentration ranges constitutes an alternative embodiment of the invention.

Numerous modifications and variations of the present invention are possible in light of the above teachings. It is therefore to be understood that within the scope of the appended claims, the invention may be practiced otherwise than as specifically described herein.

What is claimed is:

1. A method of treating steroid-induced obesity in a subject in need thereof comprising administering to the subject a therapeutically effective amount of a GLP-1 agonist for reducing body weight in said subject administered a steroid, wherein the GLP-1 agonist is $\text{Arg}^{34}\text{Lys}^{26}(N^{\epsilon}\text{-}(\gamma\text{-Glu}(N^{\epsilon}\text{-hexadecanoyl})))\text{-GLP-1(7-37)}$.

2. The method of claim 1, wherein the subject has a body mass index (BMI) of at least 30.

3. The method of claim 1, wherein the subject has a BMI of at least 27.

4. The method of claim 1, wherein the subject has a BMI of at least 25.

5. The method of claim 1, wherein the subject's weight is about 7% over ideal.

6. The method of claim 1, wherein the subject, within the past year of steroid treatment, has gained about 1, 2, 3, 4, 5, 6, or 7% body weight.

7. The method of claim 1, wherein the subject, within the past year of steroid treatment, has gained about 7% body weight.

8. The method of claim 1, wherein the subject, within the past six months of steroid treatment, has gained about 7% body weight.

9. The method of claim 1, wherein the GLP-1 agonist is administered concurrently with the daily dosage of the steroid.

10. The method of claim 1, wherein the GLP-1 agonist is administered prior to the daily dosage of the steroid.

11. The method of claim 1, wherein the GLP-1 agonist is administered after the daily dosage of the steroid.

12. The method of claim 1, wherein the GLP-1 agonist is administered to the subject prior to the onset of obesity.

13. The method of claim 1, wherein the GLP-1 agonist is administered at the start of the subject's steroid therapy.

14. The method of claim 1, wherein the GLP-1 agonist is administered in connection with a meal.

\* \* \* \* \*